United States Patent [19]

Lampe

[11] Patent Number: 5,776,896
[45] Date of Patent: Jul. 7, 1998

[54] ANALGESIC PEPTIDES FROM VENOM OF GRAMMOSTOLA SPATULATA AND USE THEREOF

[75] Inventor: Richard Alexander Lampe, Pennsville, N.J.

[73] Assignee: Zeneca Limited, London, England

[21] Appl. No.: 775,476

[22] Filed: Dec. 30, 1996

Related U.S. Application Data

[60] Provisional application No. 60/009,581, Jan. 3, 1996.

[51] Int. Cl.$^6$ .......................... A61K 38/00; A01N 37/18; A61M 21/00; C07C 245/00
[52] U.S. Cl. .................... 514/12; 514/2; 514/21; 600/26; 530/300; 530/324; 530/855; 530/858; 435/69.1
[58] Field of Search .................... 514/2, 21, 12; 600/26; 530/300, 324, 855, 858; 435/69.1

[56] References Cited

U.S. PATENT DOCUMENTS

| | | |
|---|---|---|
| 4,925,654 | 5/1990 | Jackson et al. . |
| 5,064,657 | 11/1991 | Jackson et al. . |
| 5,122,596 | 6/1992 | Phillips et al. . |
| 5,196,204 | 3/1993 | Jackson et al. . |
| 5,281,693 | 1/1994 | Jackson et al. . |

FOREIGN PATENT DOCUMENTS

WO 93/13128  7/1993  WIPO .

OTHER PUBLICATIONS

Lampe et al., "Isolation and Pharmacological Characterization of ω-Grammotoxin SIA, a Novel Peptide Inhibitor of Neuronal Voltage-Sensitive Calcium Channel Responses", Molecular Pharmacology, 44:451–460, May 18, 1993.

*Primary Examiner*—Paula K. Hutzell
*Assistant Examiner*—Khalid Masood
*Attorney, Agent, or Firm*—Liza D. Hohenschutz

[57] ABSTRACT

The present invention provides novel methods of treating pain comprising administering to a mammal in need of such treatment an effective analgesic amount of a peptide having the amino acid sequence of SEQ ID. NO.:1 or SEQ ID NO: 2. The invention further provides a purified peptide having the amino acid sequence of SEQ ID NO: 1. The peptides of SEQ ID NO.: 1 and SEQ ID NO.: 2 can also be used in methods for identifying compounds having analgesia-inducing activity.

3 Claims, No Drawings

5,776,896

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 29
        ( D ) OTHER INFORMATION: /note= "Xaa is amidated leucine"

( x i ) SEQUENCE DESCRIPTION: SEQ ID NO:1:

```
Tyr Cys Gln Lys Trp Leu Trp Thr Cys Asp Ser Glu Arg Lys Cys Cys
 1               5                  10                      15

Glu Asp Met Val Cys Arg Leu Trp Cys Lys Lys Arg Xaa
            20                  25
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Tyr Cys Gln Lys Trp Met Trp Thr Cys Asp Glu Glu Arg Lys Cys Cys
 1               5                  10                      15

Glu Gly Leu Val Cys Arg Leu Trp Cys Lys Lys Lys Ile Glu Trp
            20                  25                  30
```

1

ANALGESIC PEPTIDES FROM VENOM OF GRAMMOSTOLA SPATULATA AND USE THEREOF

This application claims the benefit of U.S. Provisional Application No. 60/009,581 filed on Jan. 3, 1996.

FIELD OF THE INVENTION

The present invention relates to peptides that induce analgesia in mammals. More particularly, the present invention relates to analgesia-inducing peptides obtainable from venom of *Grammostola spatulata*, the Chilean pink tarantula spider.

BACKGROUND OF THE INVENTION

Pain is one of the basic clinical symptoms seen by every physician and is usually categorized into three segments: mild, moderate and severe. The mild-to-moderate segment has multiple product entries including aspirin, acetaminophen, ibuprofen, and other non-steroidal, anti-inflammatory (NSAID) products. Narcotic analgesics remain the mainstay of currently marketed products for the treatment of moderate-to-severe pain.

Cancer and the post-operative surgical period are two conditions most often associated with moderate-to-severe pain. Tumor infiltration of bone, nerve, soft tissue or viscera are the most common causes of cancer pain accounting for 65–75% of patients. Pain as a result of cancer treatment from surgery, chemotherapy or radiation accounts for 15–25% of patients, with the remaining 5–10% reporting pain independent of their cancer or cancer therapy. Various factors influence the prevalence of cancer pain including the primary tumor type, stage and site of disease and patient variables, especially psychological variables. Similarly, patient response to post surgical pain is dependent upon location and extent of intervention as well as personal attributes. However, post surgical pain is distinguished from cancer pain by length of treatment period.

The major concern with narcotics, which constitute the largest segment of the U.S. market for treatment of moderate-to-severe pain, is the potential for addiction and loss of activity (i.e. tolerance) with continued use. Consequently, there is a need for other analgesics that can relieve pain, especially moderate-to-severe pain associated with caner. In order to improve analgesic responsiveness and reduce side effects, research efforts have focused on both drug delivery strategies and novel drug entities. Newer drug delivery strategies include transdermal narcotics, PCA, intraspinal implantation of controlled release pumps and implantation of encapsulated living cells which release naturally-occurring endorphins or other analgesic peptides. New drug approaches reflect the varying pathways and causes of moderate-to severe pain. Classes of compounds in development for treating pain include serotonergics, noradrenergics, opioid partial agonists and kappa opioid agonists. Therapeutic targets with significant preclinical investigation include tachykinin/bradykinin antagonists and excitatory amino acid antagonists. Newer targets being exploited include growth factors, cytokines, nitride oxide regulators, etc. Natural sources including folk medicine remedies and frog venom extracts are also under investigation.

Investigations of spider venoms for identification of biological entities with commercial potential has focused primarily on the agrochemical sector. The ultimate goal of these activities has been the search for chemical constituents which interact selectively with invertebrate species to induce paralysis and/or death with minimal mammalian toxicological properties. However, in recent years, spider venoms have joined other predator-derived venoms being exploited for identification of compounds which identify mammalian targets and which assist the development of pharmaceuticals. The arachnid species *Grammostola spatulata*, commonly referred to as the Chilean pink tarantula spider, is a member of the Theraphosidae family and the Chelicerata order. Previous studies by Lampe et al. (1993) Molecular Pharmacology 4:451–460 showed that venom of *Grammostola spatulata* contains a peptide which interacts in a non-selective manner with voltage-sensitive calcium channels.

SUMMARY OF THE INVENTION

The present invention provides methods of treating pain comprising administering to a mammal in need of such treatment an effective analgesic amount of a peptide having the amino acid sequence Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (referred to herein as GsAF I) (SEQ ID NO: 1)

or

Tyr-Cys-Gln-Lys-Trp-Met-Trp-Thr-Cys-Asp-Glu-Glu-Arg-Lys-Cys-Cys-Glu-Gly-Leu-Val-Cys-Arg-Leu-Trp-Cys-Lys-Lys-Lys-Ile-Glu-Trp (referred to herein as GsAF II) (SEQ ID NO:2).

An additional aspect of the invention provides a purified peptide having the amino acid sequence Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (GsAF I) (SEQ ID NO: 1)

A further aspect of the present invention provides pharmaceutical compositions comprising a pharmaceutically acceptable carrier or diluent and a peptide having the amino acid sequence Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (SEQ ID NO: 1)

An additional aspect of the invention provides methods for identifying compounds that mimic the analgesia-inducing activity of GsAF I and/or GsAF II.

The present invention additionally provides antibodies specific for GsAF I. The antibodies can be monoclonal or polyclonal. Antibodies can be prepared using methods known in the art such as the methods in Harlow et al. eds., *Antibodies: A Laboratory Manual*, New York, cold Spring Harbor Laboratory Press (1988).

DETAILED DESCRIPTION OF THE INVENTION

Applicant has discovered that peptides from venom of the Chilean pink tarantula spider, *Grammostola spatulata*, have analgesia-inducing properties and are thus useful as analgesics for treatment of pain in mammals, including humans, and as research tools for identification of compounds that mimic the analgesic activity of the peptides.

Thus, the present invention provides a method for treating pain comprising administering to a mammal in need of such treatment an effective analgesic amount of a peptide having the amino acid sequence Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (GSAF I) (SEQ ID NO: 1); or Tyr-Cys-Gln-Lys-Trp-Met-Trp-Thr-Cys-Asp-Glu-Glu-Arg-Lys-Cys-Cys-Glu-Gly-Leu-Val-Cys-Arg-Leu-Trp-Cys-Lys-Lys-Lys-Ile-Glu-Trp (GsAF II) (SEQ ID NO:2)

The peptides are useful for treating pain in mammals, including humans, conventional laboratory animals such as rats, mice and guinea pigs, domestic animals such as cats, dogs and horses, and any other species of mammal. The peptides can be used to treat acute or chronic pain from any source or condition, such as burns, cancer, neuropathies, organ inflammation or surgical intervention. Preferably, however, the peptides are used to treat moderate-to-severe pain due to cancer or surgery. The peptides can be administered orally, parenterally, intrathecally, topically, intraveneously, intramuscularly or intradermally/epineurally. A preferred route of administration is intrathecally.

The peptides thereof can be prepared for pharmaceutical use by incorporating them with a pharmaceutically acceptable carrier or diluent. Thus, a further aspect of the present invention provides pharmaceutical compositions comprising a peptide from *Grammostola spatulata* as described herein and a pharmaceutically acceptable carrier or diluent. The peptide can be prepared for pharmaceutical use by incorporating it in unit dosage form as tablets or capsules for oral or parenteral administration either alone or in combination with suitable carriers such as calcium carbonate, starch, lactose, talc, magnesium stearate, and gum acacia. The peptide can be formulated for oral, parenteral or topical administration in aqueous solutions, aqueous alcohol, glycol or oil solutions or oil-water emulsions. Buffered-aqueous or carrier mediated aqueous/non-aqueous intrathecal and intravenous dosages can be formulated. These and other suitable forms for the pharmaceutical compositions of the invention can be found, for example, in *Remington's Pharmaceutical Science*, 15th ed., Mack Publishing Company, Easton, Pa. (1980). The pharmaceutical compositions of the invention can comprise any combination of one or both of the peptides.

The amount of the active component (i.e. peptide) in the pharmaceutical compositions can be varied so that a suitable dose is obtained and an effective analgesic amount can be administered to the patient. The dosage administered to a particular patient will depend on a number of factors such as the route of administration, the duration of treatment, the size and physical condition of the patient, the potency of the peptide and the patient's response thereto. An effective analgesic amount of the peptide when administered intrathecally is generally in the range of from about 5 nanograms per kilogram body weight of the patient to about 500 micrograms per kilogram; preferably from about 50 nanograms per kilogram to about 50 micrograms per kilogram; more preferably from about 500 nanograms per kilogram to about 5 micrograms per kilogram. Effective amounts of the peptide will vary when administered by other routes. An effective analgesic amount can be estimated by testing the peptide in one or more of the pain tests disclosed herein to arrive at a dose that can be varied according to one or more of the criteria listed above to provide a suitable amount of the peptide to the mammal.

The terms "inducing analgesia", "analgesia-inducing activity", "analgesia-producing" and similar terms refer to the ability of the peptide to treat pain in mammals or attenuate pain as evidenced by favorable results in one or more conventional laboratory models for testing pain or assessing analgesia such as the tests set forth herein.

Analgesic activity of the peptides is determined by testing in at least one, and preferably more than one, of a series of tests which includes 1) tail flick latency (Abbott, F. V. et al., Pharmacol. Biochem. Behav., 17, 1213–1219, 1982; Cridland, R. A. and Henry, J. L., Brain Res., 584:1–2, 163–168, 1992), 2) hot plate threshold (Woolfe,G and Macdonald, A. A., JPET, 80, 300, 1944; Ankier, S. I., European J. Pharmacol., 27, 1–4, 1974), and 3) vonFrey filament threshold (Kim, S. H. et al., Pain, 55, 85–92, 1993).

The tail flick latency and hot plate threshold tests are measurements of thermal nociception. The von Frey filament threshold test evaluates mechanical nociceptive activity. All three of these pain tests evaluate the analgesic activity of compounds against the phasic stimulation of either thermal- or mechanical-nociceptors and reflect to a large degree the activation of A- and polymodal C-fiber afferents. Clinical analgesics with an opioid-based mechanism of activity are efficacious in these tests, whereas those analgesics which either interact preferentially with peripheral targets or possess multiple sites of action are generally less active. These tests are good predictors of moderate to strong analgesic agents and within the opioid class of compounds the correlation with clinical effect is good. The non-steroidal anti-inflammatory (NSAID) class of analgesics, which clinically target the lower end of the pain scale, are not routinely detected under the parameters normally used for these tests.

Analgesic detection of NSAIDs is dependent upon the generation of a nociceptive status of increased responsiveness (i.e. a lowering of threshold to noxious stimuli) in response to primary afferent tissue damage and inflammation. Interaction between the immune and nervous systems to induce this state represents the target for NSAID activity. Inhibition of this heightened activity of peripheral nociceptors, and of the corresponding central circuitry, is detected over longer time intervals by either monitoring spontaneous behavior or the response to subsequent noxious stimuli. These more chronic measurements of the "hyperalgesic" status are considered to mimic most clinical conditions of pain. They also broaden the detection capability for useful analgesic agents without exclusion of active agents detected in the phasic pain tests. Numerous pain tests have been developed to model this condition in laboratory animals. The noxious stimuli used to induce this condition are either chemical irritants/caustic agents or inflammatory stimulators. Within these tests, the major defining variable is the time interval required for the development, and the ethically justifiable duration, of the hyperalgesic/inflammatory state. Compounds can be evaluated for their intrinsic activity to prevent the development of the hyperalgesic condition (i.e. compound administered prior to noxious stimulant) or to reduce the increased nociceptive response (i.e. compound administered post-noxious stimulation) or both. Primary end points in these tests are measurements of nociceptive and inflammatory status.

The formalin test (Dubuisson, D. and Dennis, S. G., Pain, 4, 161–174, 1977) was used since it produces a well delineated bi-phasic response that is considered to be indicative of tonic versus acute pain and can be performed within a reasonably short time period (i.e. <1 hr). The initial phase of this response is triggered by a substantial primary afferent barrage, similar in character to that described for the acute phasic tests except that chemical nociceptors are the mediators. The second phase is considered to be the hyperalgesic spontaneous activity that results from the initial tissue damage and reflects the lowering of the nociceptive threshold plus the priming or "wind up" of the corresponding spinal circuitry. Hence, both peripheral and central neuronal circuits and mediators are required to induce and sustain this painful tissue-injury condition.

The formalin model in rodents has been validated as a predictive test of treating injury-induced pain in humans (Dennis, S. G. and Melzack, R., In: Advances in Pain Research and Therapy, vol. 3, 747–759, Eds. J. J. Bonica et al., Raven Press:New York, 1979; Tjolsen, A. et al., Pain, 51: 5–17, 1992.). Evaluation of clinically used analgesics in this model has consistently demonstrated a strong correlation with human efficacy for opioid based compounds or drugs known to interact with opioid systems (Wheeler-Aceto, H., "Characterization Of Nocioception And Edema After Formalin-Induced Tissue Injury In The Rat: Pharmacological Analysis Of Opioid Activity", Doctoral Dissertation, Temple School of Medicine, Philadelphia, Pa., 1994; Shibata, M. et al, 38, 347–352, 1989). Efficacy and potency profiles for milder analgesic drugs possessing primarily NSAID based mechanisms of action have produced equivocal results (Wheeler-Aceto, H., Doctoral Dissertation, Temple School of Medicine, Philadelphia, Pa., 1994; Hunskaar, S. et al., Neurosci. Meth., 14, 69–76, 1985; Shibata, M. et al., Pain, 38, 347–352, 1989; Malmberg, A. B. and Yaksh, T. L., J. Pharmacol. Exp. Ther., 263, 136–146, 1992). These equivocal findings in the formalin model reflect experimental differences in how the test is conducted such as the parameters of the test (i.e. stimulus intensity administered, response measurement and response interval analyzed), species and strain of laboratory animal used and route/timing of administration of compounds (for review, Wheeler-Aceto, H., Doctoral Dissertation, Temple School of Medicine, Philadelphia, Pa., 1994). However, consensus exists that high efficacy analgesics used to treat moderate to severe pain are detected in this test independent of these experimental differences. If these compounds have limited central nervous system penetration, less activity is detected.

In addition to their use as analgesics, the peptides are useful in biological assays such as assays to detect compounds that mimic the analgesic activity of the peptides, assays to detect the anatomical site of action of the peptides, or studies on the mechanism of action of the peptides. Thus, another aspect of the invention provides methods for detecting compounds that mimic the analgesic activity of GsAF I and/or GsAF II. Mimicking the activity of the peptides disclosed herein refers to the ability of test compounds to induce analgesia, bind to cellular receptors to which the peptides bind or otherwise act in the same or similar physiological manner as the peptides. Thus, the present invention provides methods for identifying compounds having analgesia-inducing activity or which otherwise mimic the activity of GsAF I and/or GsAF II comprising the steps of adding a test compound to a biological assay that determines activity of a peptide having the amino acid sequence of SEQ ID NO: 1 or SEQ ID NO: 2; and detecting the activity of the test compound.

Biological assays to identify compounds that mimic the activity of GsAF I and/or II can be in vivo assays, such as those described herein, or in vitro assays, such as the assays described below. For example, GsAF I and/or GsAF II can be used in competitive binding screening assays to identify compounds that mimic the activity of GsAF I and II according to the following method. A test compound and detectably labeled peptide are added to mammalian cells or tissue under conditions that allow binding to the cells or tissue. Binding of labeled peptide to the mammalian cells or tissue is then measured. Compounds that mimic the activity of the detectably labeled peptide will compete with the peptide for binding sites on the receptor. Consequently, a smaller amount of detectable label will be measured when the test compound mimics the activity of the peptide by binding to the receptor than when the test compound does not mimic the activity of the peptide and does not bind to the receptor, or does so with much less affinity. In particular, GsAF I and/or II could be labeled with $^{125}I$ and used in the assay described in Stumpo et al, Eur. J. Pharmacol. 206:155, 1991 and modified from Abe et al, Neurosci. Lett. 71:203, 1986. Briefly, individual test compounds are preincubated with brain or spinal cord membrane tissue prior to the addition of $^{125}I$-labeled GsAF I and/or II, followed by incubation to allow binding to occur. The reaction mixture is then filtered and the filters containing the brain or spinal cord membrane tissue are rinsed with buffer. Binding of $^{125}I$-labeled peptide can be determined by scintillation counting. Compounds that mimic the action of GsAF I and II will compete with the labeled peptide and produce lower levels of labeled peptide binding to the receptor on the cells of the brain or spinal cord membrane tissue than compounds that do not mimic the activity of GsAF I or II. Nonspecific binding will be defined as that remaining in the presence of excess (100–1,000X) unlabeled GsAF I or GsAF II.

For use as a reagent in biological assays, the peptides preferably incorporate a detectable label. The detectable label can be any conventional type of label and is selected in accordance with the type of assay to be performed. For example, the detectable label can comprise a radiolabel such as $^{14}C$, $^{125}I$, or $^3H$, an enzyme such as peroxidase, alkaline or acid phosphatase, a fluorescent label such as fluoroisothiocyanate (FITC) or rhodamine, an antibody, an antigen, a small molecule such as biotin, a paramagnetic ion, a latex particle, an electron dense particle such as ferritin or a light scattering particle such as colloidal gold. Suitable method to detect such labels include scintillation counting, autoradiography, fluorescence measurement, calorimetric measurement or light emission measurement. Detectable labels, procedures for accomplishing such labeling and detection of the labels are well known in the art and can be found, for example, in *An Introduction to Radioimmunoassays and Related Techniques: Laboratory Techniques in Biochemistry and Molecular Biology*, 4th Ed., T. Chard, Elsevier Science Publishers, Amsterdam, The Netherlands, 1990; *Methods in Non-Radioactive Detection*, Gary C. Howard, Ed., Appleton and Lange, East Norwalk, Conn., 1993 or *Radioisotopes in Biology: A Practical Approach*, R. J. Slater, Ed., IRL Press at Oxford University Press, Oxford, England, 1990.

Additionally, the peptides can be used in the assay of Keith et al, J. Auton. Pharmacol., 9:243–252, 1989 and Mangano et al, Eur. J. Pharmacol. 192:9–17, 1991 to identify compounds that mimic the activity of GsAF I or II. Briefly, this assay measures $K^+$- evoked release of $^3H$-D-aspartate and $^3H$-norepinephrine from rat brain or spinal cord slices. Spinal cord or brain slices can be pre-equilibrated with GsAF I/GsAF II, test compound or vehicle for 15 min prior to $K^+$ stimulation. Levels of $K^+$-induced release of $^3H$-norepinephrine and $^3H$-D-aspartate are measured. Inhibition of $K^+$-induced release of $^3H$-norepinephrine and $^3H$-D-aspartate by GsAF I/GsAF or test compound versus inhibition due to the vehicle control is then determined. Test compounds can be screened to determine both absolute inhibitory activity as well as activity relative to GsAF I/GsAF II.

The compounds that mimic the analgesic activity of GsAF I and/or II will themselves have analgesic activity and can be used as analgesics or for other purposes such as determining the anatomical site of action, determining the mechanism of action of the peptides and in screening assays to identify other compounds that mimic the analgesic activity of the peptides. Preferably test compounds used in the screening assay are small organic molecules but analgesic activity of any type or size of compound such as proteins and peptides can also be tested with the methods of the invention.

GsAF I and/or II can be used in assays to identify its site of action and for further physiological characterization of its activity. For example, the peptides can be used to study inhibition of binding/interaction of labelled ligand to mammalian tissues, isolated cells or subcellular components derived therefrom. Similarly, the peptides can be used to study inhibition of binding/interaction of labelled ligand to specific recombinantly expressed proteins generated following either cDNA or genomic transformations/transfections of eukaryotic or prokaryotic host systems. The peptides can be used to study analogous biochemical interaction with mammalian tissue function to include receptor mediated activation/inhibition of specified transduction pathways, movement of ionic species across biological membranes and alteration of transcriptional/translational profile of specific pain-induced gene activity. Specifically, methods to measure the alteration of potassium, sodium, calcium, chloride or hydrogen ionic distribution across mammalian cell derived membrane barriers as measured by either radioisotopic or fluorescent detection of specified ionic species can be utilized. The effects of these ionic movements upon the regulation of specific immediate early genes can be studied as well.

The peptides can additionally be used for electrophysiological measurements of potassium, sodium, calcium and chloride distribution across mammalian cell membranes to include macroscopic analysis of synaptic transmission as well as microscopic analysis of specified ionic currents. Specifically, inhibition of noxious-mediated neuronal firing and synaptic transmission within spinal dorsal horn neurons can be analyzed as well as inhibition of isolated specific ionic currents within individual dorsal root ganglion or spinal dorsal horn neurons.

The peptides can further be used in studies of inhibition of physiological response to nociofensive/noxious stimuli administered to mammalian species. Specifically, motor parameters (i.e. limb withdrawal thresholds or response time latencies/durations) can be quantitated in response to either thermal, mechanical or chemical noxious stimuli administered to either naive animals or animals in which a painful condition has been experimentally induced.

GsAF I and II can be prepared by isolation from *Grammostola spatulata* venom, chemical synthesis or recombinant DNA methods. *Grammostola spatulata* venom is commercially available from Spider Pharm, Feasterville, Pa., USA. The peptides are preferably isolated from spider venom by sequential fractionation using reverse phase-high pressure liquid chromatography on C-8 and C-18 silica supports with trifluoroacetic acid/acetonitrile buffer. A preferred C-8 silica support is Zorbax® Rx C-8 (Mac-Mod Analytical, Inc., West Chester, Pa.) which is comprised of 5 micron diameter silica particles having 300 Å pore size and covalently modified to contain diisopropyloctyl side chains. The C-18 silica support is preferably comprised of 5 micron diameter silica particles having 300Å pore size and covalently modified to contain an octadecyl side chain. Other types of C-8 and C-18 silica supports are also suitable for use in isolating the peptides. A preferred buffer is 0.1% trifluoroacetic acid in acetonitrile. In a preferred method, crude venom is initially fractionated on a C-8 semi-preparative column using a broad 20–50% gradient of 0.1% trifluoroacetic acid in acetonitrile buffer. The peptides are further purified using a C-8 column and shallower gradients of the same buffer, followed by additional fractionation using a C-8 column and the broad buffer gradient.

GsAF I and II can be prepared by recombinant DNA techniques. A DNA sequence coding for one of the peptides is prepared, inserted into an expression vector and expressed in an appropriate host cell. The peptide thus produced is then purified from the host cells and/or cell culture medium. Methods for preparing DNA coding for the peptides and expression of the DNA are well-known and can be found, for example, in Sambrook et al. (1989) *Molecular Cloning: A Laboratory Manual*, Cold Spring Harbor, N.Y.: Cold Spring Harbor Laboratory Press, *Guide to Molecular Cloning Techniques: Methods in Enzymology*, vol.152, S. L. Berger and A. R. Kimmel, Ed., Academic Press (San Diego, Calif.), 1987 and *Gene Transfer and Expression Protocols: Methods in Molecular Biology* vol.7, E. J. Murray, Ed., Humana Press (Clifton, N.J.), 1991.

The peptides can also be prepared by chemical synthesis using either automated or manual solid phase synthetic technologies. These techniques are well known in the art and are differentiated on the basis of features such as selection of synthetic resin backbone, selection of amino, carboxyl and side chain protecting groups and selection of deprotection strategies. Methods for synthesizing peptides can be found in standard texts such as E. Atherton and R. C. Sheppard, *Solid Phase Peptide Synthesis: A Practical Approach*, IRL Press/Oxford University Press, Oxford, UK, 1989 and M. Bodanszky, *Peptide Chemistry: A Practical Textbook*, Springer-Verlag, New York, USA, 1988.

In a preferred synthetic method, synthesis of GsAF I and GsAF II can be done using Fmoc chemistry on an automated synthesizer. Dependent upon quantitative yields, production of the linear reduced peptide can be performed in either a single process or in two different processes followed by a condensation reaction to join the fragments. A variety of protecting groups can be incorporated into the synthesis of linear peptide to facilitate isolation, purification, and/or yield of the desired peptide. Protection of cysteine residues found in the peptide can be accomplished using, for example, a triphenylmethyl, acetamidomethyl and/or 4-methoxybenzyl group in any combination. Such a strategy may offer advantages for subsequent oxidation studies to yield folded peptide. Differential proteolytic digestion of native GsAF I and GsAF II coupled to mass spectrometric analysis of the resultant fragments can be utilized for assignment of intramolecular disulfide bonds. This data can be subsequently incorporated into synthetic peptide strategies to increase yields. Oxidative strategies include random air oxidation, iodine assisted oxidation, and dimethylsulfoxide assisted oxidation, as well as the use of small quantities of thiol reagents in an oxidation reaction to attain the desired folded peptide. Crude, linear, reduced peptides, as well as homogeneous, oxidized peptides, can be purified using reverse-phase high pressure liquid chromatography HPLC (RP-HPLC) or other standard techniques.

A further aspect of the invention provides a novel peptide which has the amino acid sequence
Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (GsAF I) (SEQ ID NO: 1)

The leucine at the carboxy terminus of the peptide is amidated, i.e., the free end of the terminal leucine residue ends with —CO—$NH_2$ instead of —COOH. Both amidated and non-amidated peptides are within the scope of the present invention.

As used herein, a purified or isolated peptide refers to a peptide that is substantially free of contaminating cellular components, other venom constituents or other material such as reagents used in chemical synthesis of the peptide.

Preferably, the peptide is present in a mixture containing the peptide in an amount greater than about 50% of the total mixture, more preferably in an amount greater than about 80%, most preferably in an amount greater than about 90%.

EXAMPLES

Example 1

Isolation and Characterization of Peptide GsAF I from Venom of *Grammostola spatulata*

A. Isolation of Peptide

Crude *Grammostola spatulata* venom was supplied as frozen aliquots by Spider Pharm, Inc. (Feasterville, Pa. 19053). Reverse phase-high pressure liquid chromatography (RP-HPLC) of the venom was performed using C-8 semi-preparative (25 cm×9.4 mm) and analytical (25 cm×4.6 mm) columns (Zorbax® RX-C8, Mac-Mod Analytical, Inc. West Chester, Pa., which is comprised of 5 micron silica microsphere particles having a 300Å pore size and covalently modified with diisopropyl octyl side chains); and a C-18 analytical (25 cm.×4.6 mm) column (Vydac, Hesperia, Calif., which is comprised of 5 micron silica microsphere particles having a 300Å pore size and covalently modified with octadecyl side chains). Semi-preparative scale RP-HPLC was done using a five milliliter per minute flow rate whereas a one milliliter per minute flow rate was used for the analytical analyses.

Detection of eluting entities was monitored via ultraviolet spectroscopy at 215 nm and fractions were either collected at 1 minute intervals or manually based upon ultraviolet intensity. Initial injection volumes of 30–50 microliter crude venom were made. Consequently, multiple fractionations were carried out at each stage of the purification with pooling of individually identical fractions. All fractions were lyophilized prior to resuspension in HPLC grade $H_2O$ for subsequent purification or in vivo analgesic testing. Resuspension volumes were based upon original crude venom volumes. Analgesic evaluation was done on samples deemed to be greater than 90% homogeneous by RP-HPLC. Samples were stored at 4 C. following resuspension. No detectable loss of activity was witnessed with storage or with adherence to either plastic or glass.

Initial fractionation of crude *Grammostola spatulata* venom on the Zorbax® RX-C8 semipreparative column was done with a 20–50% gradient of $TFA/CH_3CN$ Buffer (0.1% trifluoroacetic acid in acetonitrile) over 30 minutes with a 3 minute delay. ($TFA/CH_3CN$ Buffer was prepared by adding 4 ml of trifluoroacetic acid to 4 liters of acetonitrile.) Column flow rate was 5 milliliters per minute and fractions collected at one minute intervals. Fraction 18 was highly enriched for GsAF I. Fraction 17 also contained GsAF I peptide but in smaller quantities than fraction 18 with most purifications. Following lyophilization and resuspension of fraction 18, and optionally fraction 17, further separations were performed with shallower gradients of $TFA/CH_3CN$ Buffer.

Fraction 18 (and optionally 17) were applied to a Zorbax® (RX-C8 semi-preparative column and fractionated using a 24–30% gradient of $TFA/CH_3CN$ Buffer over 24 minutes, with 3 minute delay. The major UV absorbing peak was manually collected with removal of peak tails. After this step, sample purity was usually found to be at least 85%.

The major UV absorbing peak collected in the previous step was further purified using a 20–50% gradient of $TFA/CH_3CN$ Buffer on a Zorbax® RX-C8 semi-preparative column (flow rate 5 ml/min) over 30 min with a 3 minute delay. The primary peak which elutes at 22 minutes was collected manually with removal of peak tails. GsAF I sample purity was found to be about 98% pure.

On occasion, exposure of the GsAF I sample to a very shallow gradient of 48–51% $TFA/CH_3$ OH buffer on a Zorbax® RX-C8 semi-preparative column over 21 minutes, followed by lyophilization, resulted in the appearance of two RP-HPLC resolvable peptides that differ in mass by 16 Daltons. From internal studies done with another peptide sample, this mass differential does not translate into a differential primary amino acid sequence but most likely reflects a side-chain adduct.

B. Characterization of Peptide

1. Electrospray Mass Spectrometry (ES-MS) Analysis of Molecular Weight and Disulfide Bridge Assignment:

Electrospray spectra were acquired for the peptide using a mass spectrometer (VG/Fisons QUATTRO, Fisons Instruments, Inc. Manchester, UK) in the continuum acquisition mode. The $(M+3H)^{3+}$, $(M+4H)^{4+}$ and $(M+5H)^{5+}$ charge states were observed for each sample and mathematically transformed to yield a zero charge state spectrum. Analyses were performed on both the native/oxidized and the reduced state of the peptide. Lyophilized GsAF I was reduced in 0.5M dithio-threitol (DTT) 0.1M N-ethylmorpholine, pH 8.5, at 38 C. for 10 min. Flow injections containing approximately 200–400 picomoles of peptide were measured. The average molecular weight of GsAF I was determined to be 3707.5 Daltons (Da). After thiol reduction, the average molecular weight was measured at 3713.5 Daltons. Since each reduction of a disulfide bond increases the mass of a peptide by 2 Da, the peptides contain three disulfide linkages based upon the 6 Da mass shift.

The native oxidized peptide was digested with a combination of modified trypsin (Boehringer Mannheim) and endoproteinase Asp-N proteases. The resulting mixture of proteolysis products was subjected to liquid chromatography-electrospray mass spectral analysis to assign disulfide linkage. Multiple peptides containing a disulfide bridge linking amino acids 9 and 21 of the GsAF I peptide were observed. Scrambling of disulfide bonds may occur when proteolysis is performed at pH 8; however, randomization of proteolysis products was not observed, and disulfide bond scrambling is thought to be unlikely in this case. Links for the remaining disulfide bridges were not established. Subsequent analysis of the crude proteolysis mixture by matrix-assisted laser desorption ionization—time-of-flight (MALDI-TOF) mass spectrometry (VG Analytical/Fisons TOFSpec-SE, Fisons Instruments, Inc. Manchester, UK) provided confirmation of the electrospray mass spectral measurements.

2. N-terminal Sequence Analysis of Reduced, Pyridylethylated Native Peptides and Proteolytically Digested Fragments:

N-terminal sequencing was performed on a gas phase sequencer (Applied Biosystems 475, Foster City, Calif.). SDS-Page was performed using a 16.5% high cross linked Tris-Tricine gel (Schagger,H. and G. von Jagow, Anal. Biochem. 166:368–379, 1987) and electroblotted to ProBlot (Applied Biosystems, Foster City, Calif.)) as described by Matsuidara, P., J. Biol. Chem. 262:10035–10038. Electroblotted bands were pyridylethylated in the gas phase according to the method described in Andrews, P. C. and J. E. Dixon, Anal. Biochem. 161:524–528, 1987. Covalent attachment of peptides via activation of carboxyl groups and reaction with arylamine derivatized polyvinylidene difluoride using sequalon membranes (Millipore, Inc., Milford, Mass.) was performed according to the manufacturer's instructions. V8 proteolytic digestion of reduced (100x dithiothreitol vs. Cys on mole basis) GsAF I peptide was done in 50 mM Na phosphate buffer, pH 7.8, for 18 hr. using an enzyme:substrate ratio of 1:44. Fragments were isolated using RP-HPLC and their mass analyzed using laser desorption/ionization mass spectrometry prior to sequence analysis. Samples were applied to the sequencer either as direct solutions onto a coated disc or as covalent coupled entities to ascertain carboxyl terminal acidification/amidation. Shown below is the sequence obtained for peptide GsAF I. Amidation of the GsAF I peptide is supported by the ES-MS data for the intact, native peptide and for the respective V8 (or tryptic as well) carboxyl terminal fragment.

The sequence obtained for peptide GsAF I is

Tyr-Cys-Gln-Lys-Trp-Leu-Trp-Thr-Cys-Asp-Ser-Glu-Arg-Lys-Cys-Cys-Glu-Asp-Met-Val-Cys-Arg-Leu-Trp-Cys-Lys-Lys-Arg-Leu-NH2 (SEQ ID NO: 1)

Leu-NH2 denotes that the terminal leucine residue is amidated, i.e., the free end of the terminal leucine residue ends with —C(=O)—NH$_2$ instead of —COOH. The amino acid sequence of the peptide is presented starting with the amino terminus.

3. UV Spectroscopy:

A complete spectrum was obtained for the peptides using a 8452A diode array spectrophotometer (Hewlett Packard, Avondale, Pa., USA). Concentrations of the final peptides were deduced from the $Abs_{280nm}$. Based upon the differential contributions from 3 Trp, 1 Tyr and 6 Cys, the calculated molar extinction coefficient of GsAF I at 280 nm is 18710. In cases where sufficient peptide was isolated for accurate mass weighing (and assuming appropriate peptide content as a result of the TFA salt), the respective concentration values were in good agreement. Using either method of quantitation, and multiple preparations of native GsAF I, the venom concentration of GsAF I is estimated to be approximately 500–750 µM.

Example 2

Isolation and Characterization of Peptide GsAF II

A. Isolation of Peptide

Crude Grammostola spatulata venom was supplied, as frozen aliquots, by the commercial vendor Spider Pharm, Inc. (Feasterville, Pa. 19053). Reverse phase-high pressure liquid chromatography (RP-HPLC) of the venom was performed using Zorbax® Rx-C8 semi-preparative (25 cm×9.4 mm) and analytical (25 cm×4.6 mm) columns (Mac-Mod Analytical, Inc. West Chester, Pa.; Zorbax® Rx-C8 is comprised of 5 micron silica microsphere particles having a 300Å pore size and covalently modified with diisopropyl octyl side chains) and a C-18 analytical (25 cm×4.6 mm) column (Vydac, Hesperia, Calif.; the C-18 support is comprised of 5 micron silica microsphere particles having a 300Å pore size and covalently modified with octadecyl side chains). Semi-preparative scale RP-HPLC was done using a 5 milliliter/minute flow rate whereas a 1 milliliter per minute flow rate was used for the analytical analyses.

Detection of eluting entities were monitored via ultraviolet (UV) spectroscopy at 215 nm and fractions were either collected at 1 minute intervals or manually based upon UV intensity. Initial injection volumes of 30–50 microliter (µl) crude venom were made. Consequently, multiple fractionations were carried out at each stage of the purification with pooling of individually identical fractions. All fractions were lyophilized prior to resuspension in HPLC grade H$_2$O for subsequent purification or in vitro testing. Resuspension volumes were based upon original crude venom volumes. Evaluation was done on samples deemed to be greater than 90% homogeneous by RP-HPLC. Samples were stored at 4° C. following resuspension. No detectable loss of activity was witnessed with storage or with adherence to either plastic or glass.

Initial fractionation of crude Grammostola spatulata venom on the Zorbax® RX-C8 semi-preparative column was done with a 20–50% gradient of TFA/CH$_3$CN Buffer (0.1% trifluoroacetic acid in acetonitrile) over 30 min with a 3 minute delay. (TFA/CH$_3$CN Buffer was prepared by adding 4 ml of trifluoroacetic acid to 4 liters of acetonitrile). Column flow rate was 5 milliliters per minute and fractions collected at one minute intervals. Fraction 19 was highly enriched for GsAF II. Following lyophilization and resuspension of fraction 19, further separations of this fraction were performed with shallower gradients of TFA/CH$_3$CN Buffer.

Fraction 19 was applied to a Zorbax® RX-C8 semi-preparative column and fractionated using either a 29–33% or a 30–34% gradient of TFA/CH$_3$CN Buffer over 24 minutes with a 3 minute delay. The major UV absorbing peak was manually collected with removal of peak tails. After this step, sample purity was usually found to be at least 85%. The major UV absorbing peak was further purified using a 20–50% gradient of TFA/CH$_3$CN Buffer over 30 min with a 3 minute delay. The primary peak which elutes at 23.5 minutes was collected manually with removal of peak tails. GsAF II sample purity was found to be about 98% pure.

B. Characterization of Peptide

The peptide GsAF II was characterized using the methods described for peptide GsAF I in Example 1. The average molecular weight of GsAF II was determined to be 3979.9 Daltons (Da). After thiol reduction, the average molecular weight was 3985.9 Da. Since each reduction of a disulfide bond increases the mass of a peptide by 2 Da, the peptide contains three disulfide linkages based upon the 6 Da mass shift.

Amino acid composition analyses were performed using an amino acid analyzer (Applied Biosystems 420H, Foster City, Calif.). Data normalization was done with respect to leucine. No discrepancies (excluding those residues which are either partially or totally destroyed during hydrolysis) in residue/mol values were recorded with respect to the Edman N-terminal sequencing analysis.

Amino acid composition analysis yielded the data presented in the table below. Since tryptophan is completely destroyed and cysteine is partially destroyed in this analysis, their presence was inferred from UV spectroscopy and electrospray mass spectral analysis, respectively. Residue/mol values were calculated on the basis of using Leu as the standard.

| Residue | Total Amount (pmole) | Residue/mol |
|---------|---------------------|-------------|
| Asp/Asn | 701.2 | 1.2 |
| Glu/Gln | 2767.6 | 4.7 |
| Ser | 108.9 | 0.2 |
| Gly | 618.1 | 1.0 |
| His | 0 | — |
| Arg | 1050.0 | 1.8 |
| Thr | 518.9 | 0.9 |
| Ala | 35.5 | 0.1 |
| Pro | 36.7 | 0.1 |
| Tyr | 547.5 | 0.9 |
| Val | 523.9 | 0.9 |
| Met | 875.7 | 1.5 |
| Cys | 2124.1 | 3.6 |
| Ile | 545.3 | 0.9 |
| Leu | 1186.1 | 2.0 |
| Phe | 48.5 | 0.1 |
| Lys | 2639.7 | 4.5 |

Shown below is the amino acid sequence for the peptide GsAF II:

Tyr-Cys-Gln-Lys-Trp-Met-Trp-Thr-Cys-Asp-Glu-Glu-Arg-Lys-Cys-Cys-Glu-Gly-Leu-Val-Cys-Arg-Leu-Trp-Cys-Lys-Lys-Lys-Ile-Glu-Trp (SEQ ID NO:2)

Deduction of Trp at position 31 of GsAF II is based upon amino acid compositional data and ES-MS analysis. Specifically, the unaccounted mass difference between the calculated mass value for the Edman deduced sequence and the mass spectral analysis for the native peptide is 186 Da assuming a free acid carboxyl terminus or 187 Da if the carboxyl terminus is amidated. This mass difference (+ or −1 Da) could be accounted for by multiple amino acid combinations. However, none of those combinations are in good agreement with the amino acid composition data. Since the mass of an internal Trp is 186 Da, and Trp is destroyed under the hydrolysis conditions, assignment of Trp to position 31 as a free acid was tentatively made. This assignment was subsequently supported by analysis of the carboxyl fragment of GsAF II isolated following tryptic digestion. Both high resolution mass spectral analysis and MS—MS sequencing analysis of the fragment demonstrate the presence of a free acid Trp at the carboxyl terminus. These data were further corroborated when identical analyses were obtained for a synthetically prepared Lys-Ile-Glu-Trp peptide. Additionally, the RP-HPLC retention profile of both the native fragment and the synthetic fragment were identical.

Based upon the presence of 4 Trp, 1 Tyr and slight contribution from 6 Cys residues, a molar extinction coefficient of 24310 at 280 nm was deduced for GsAF II. Using this value, UV spectroscopy analyses of native GsAF II preparations indicate that the venom concentration of this peptide is approximately 3–5 mM.

Example 3

Analgesic Evaluation - Tail Flick Latency

This test measures the time interval required for a rat to withdraw its tail, via a spinally mediated reflex mechanism, from a high intensity light source (IITC Inc./ Life Sciences Instruments, Woodland Hills, Calif. 91367) focally applied to the dorsal surface of the appendage. The intensity of the light beam has been experimentally defined such that naive animals will withdraw their tails within 2 to 4 seconds. A maximum cut off time for the light source has been set at ten seconds to reduce the amount of secondary tissue damage.

Data is expressed either as absolute time or a percentage of the maximal possible effect (MPE) which is described by the following equation where 10 seconds is the maximum:

$$\% MPE = \frac{(\text{post-treatment latency} - \text{pretreatment latency})}{10 - \text{pretreatment latency}}$$

(Latency refers to the amount of time before the animal removed its appendage from the light source.)

GsAF I Administration:

With minimal restraint, peptide GsAF I was injected intrathecally (i.th.) into young (75–150 gram) male Sprague-Dawley rats (Charles Rivers Laboratories, Wilmington, Mass. 01887). I.th. injections were made into the spinal subarachnoid space between lumbar spinous processes L4 and L5 using 10 microliter Hamilton syringes equipped with ⅝ inch by 28G needles. Dosing levels were based upon concentrations deduced from ultraviolet absorbance values at 280 nm using an extinction coefficient of 18710. Injection volume was 10 microliters. The injection vehicle was saline or 0.1% bovine serum albumin(BSA)/saline. The rats were pretreated with GsAF I 30 minutes prior to exposure to the light source.

Complete inhibition of the tail flick response (i.e., latency value greater than 10 seconds) was recorded in most rats following administration of 180 picomoles (666 nanograms) of GsAF I. A 95% MPE was attained for this dose and confounding side effects such as motor disturbances, limb impairment/paralysis, righting reflex, sedation, etc.) were either minimal or not present. Logarithmic decreases in the dose resulted in rapid loss of effect. 18 picomoles (66 nanograms) of GsAF I produced 29% MPE and 1.8 picomoles (6.6 nanograms) was inactive. Maximal activity was detected with a 30 minute pretreatment time.

GsAF II Administration:

With minimal restraint, peptide GsAF II was injected intrathecally (i.th.) into young (75–150 gram) male Sprague-Dawley rats (Charles Rivers Laboratories, Wilmington, Mass.)) into the spinal subarachnoid space between lumbar spinous processes L4 and L5 using 10 microliter Hamilton syringes equipped with ⅝ inch by 28G needles. Dosing levels were based upon concentrations deduced from ultraviolet absorbance values at 280 nm using the deduced molar extinction coefficient of 24310. Injection volume was 10 microliters. The injection vehicle was saline or 0.1% bovine serum albumin(BSA)/saline. The rats were pretreated with GsAF II 15 minutes prior to exposure to the light source.

Complete inhibition of the tail flick response (i.e. latency greater than ten seconds) was recorded with all animals (n=8) dosed with 2.33 nanomoles (9.27 micrograms) of GsAF II. When animals were dosed with 583 picomoles (2.33 micrograms) of GsAF II, 100% MPE was recorded for five of six animals, with the average MPE at this dose of 92%. Similar to GsAF I, no confounding side effects were detected at these doses.

Example 4

Analgesic Evaluation - Hot Plate Threshold

This test measures the temperature at which point a rat voluntarily removes one of its hindlimbs from the heated surface and either shakes or lick the affected appendage. The temperature of the heated surface is pre-set to the experimentally deduced value of 38 C. and a maximum cutoff value of either 53 C. or 54 C. has been used. Data is expressed either as absolute temperature in degrees C. or as percentage maximal possible effect as described by the formula $$\% MPE = \frac{(\text{postlatency value} - \text{prelatency value})}{53 - \text{prelatency value}}$$

(54 is substituted for 53 in the above formula if it is the maximal value.)

GsAF I Administration:

With minimal restraint, peptide GsAF I was injected intrathecally (i.th.) into young (75–150 gram) male Sprague-Dawley rats (Charles Rivers Laboratories, Wilmington, Mass.) into the spinal subarachnoid space between lumbar spinous processes L4 and L5 using 10 microliter Hamilton syringes equipped with ⅝ inch by 28G needles. Dosing levels were based upon concentrations deduced from ultraviolet absorbance values at 280 nm using an extinction coefficient of 18710. Injection volume was 10 microliters. The injection vehicle was saline or 0.1%bovine serum albumin(BSA)/saline. The rats were pretreated with GsAF I 30 minutes prior to exposure to heat.

With a 30 minute pretreatment interval, 180 picomoles of GsAF 1 (666 nanograms) produced a 70% MPE. Lowering the dose ten-fold (to 18 picomoles) resulted in the loss of significant activity. Greater efficacy at multiple doses could be obtained with one hour pretreatment. With one hour pretreatment, a 180 picomole (66 nanograms) dose of GsAF I produced a 91% MPE and 18 picomoles (6.6 nanograms) produced a 24% MPE. No adverse motor effects were evident at these doses. This is corroborated by the observation that the animals' front paws were responsive at sub threshold temperatures and were quickly lifted off the hot surface at the elevated temperatures.

GsAF II Administration:

With minimal restraint, peptide GsAF II was injected intrathecally (i.th.) into young (75–150 gram) male Sprague- Dawley rats (Charles Rivers Laboratories, Wilmington, Mass.) into the spinal subarachnoid space between lumbar spinous processes L4 and L5 using 10 microliter Hamilton syringes equipped with ⅛ inch by 28G needles. Dosing levels were based upon concentrations deduced from ultraviolet absorbance values at 280 nm using an extinction coefficient of 187 10. Injection volume was 10 microliters. The injection vehicle was saline or 0.1% bovine serum albumin(BSA)/saline. The rats were pretreated with GsAF II 15 minutes prior to exposure to heat.

A 100% MPE was recorded for all animals receiving a 2.33 nanomole (9.27 micrograms) dose of GsAF II. When the dose was lowered to 583 picomoles (2.32 micrograms) , an average MPE of 59% was recorded. No motor coordination problems were witnessed at these doses.

Example 5

Analgesic Evaluation - von Frey Threshold

In this test filaments of increasing thickness are applied to the dorsal surface of a hindlimb until the rat either voluntarily removes the appendage with a forcible escape movement or vocalizes. The thickness of the filaments are arbitrarily labelled with a value which can be transformed into a grams force reading according to the following equation:

$$\text{grams force} = \frac{10^{(\text{von Frey score}-1)}}{1000}$$

Data are expressed either as absolute gram force values or a percentage of the maximum possible effect (MPE) as described in the following equation:

$$MPE = \frac{(\text{postlatency value} - \text{prelatency value})}{446.7 - \text{prelatency value}}$$

GsAF I Administration:

When tested 30 minutes post injection, doses of 180 picomoles (666 nanograms) and 18 picomoles (66 nanograms) of GsAF I produced 93% and 24% MPE's, respectively. Extending the pretreatment period to one hour resulted in a 100% MPE for the 180 picomole dose and a 22% MPE for the 18 picomole (6.6 nanograms) dose. No confounding side effects were present.

GsAF II Administration:

When tested 30 minutes post injection, a 2.33 nanomole (9.27 micrograms) dose of GsAF II produced an MPE of 83%. A 583 picomole (2.32 micrograms) dose of GsAF II produced an MPE of 48%. At the higher dose, 75% of the rats tested demonstrated maximal analgesic activity (i.e. 100% MPE). Based upon the GsAF I data, it is assumed that greater analgesic efficacy with GsAF II would be obtained if longer pretreatment were used.

Example 6

Analgesic Evaluation - Formalin Pain Test

The noxious stimulus for this test is the sub-cutaneous injection of a 5% solution of formalin into the dorsal surface of one of the hindlimbs of the animal. Motor activity indices used in this test are 1) the total time spent licking that appendage and 2) the total number of flinching/shaking responses of the affected appendage. Data collection is initiated immediately upon injection of the formalin solution into the limb. The acute phase response is defined by the time interval of 0–5 minutes post formalin injection. The tonic phase response is defined by the interval of 20–35 minutes post formalin injection Data collection is done in a computerized format. Expression of the data is done using either absolute values or as percent control which is defined by the level of response following injection of saline vehicle.

GsAF I Administration:

With minimal restraint, peptide GsAF I was injected intrathecally (i.th.) into young (75–150 gram) male Sprague-Dawley rats (Charles Rivers Laboratories, Wilmington, Mass.) into the spinal subarachnoid space between lumbar spinous processes L4 and L5 using 10 microliter Hamilton syringes equipped with ⅛ inch by 28G needles. Dosing levels were based upon concentrations deduced from ultraviolet absorbance values at 280 nm using an extinction coefficient of 18710. Injection volume was 10 microliters. The injection vehicle was saline or 0.1% bovine serum albumin(BSA)/saline. The rats were pretreated with GsAF I 30 minutes prior to injection with the formalin solution.

The following results were obtained 30 minutes post injection of 180 picomoles (666 nanograms) 18 picomoles (66 nanograms) and 1.8 picomoles (6.6 nanograms) of GsAF I. Values are presented as % control with absolute levels in parentheses.

|  | Acute Flinches | Tonic Flinches | Tonic Licking |
| --- | --- | --- | --- |
| Control | (42.5) | (139) | (181.8 sec) |
| 180 pmoles | 8.9% (3.8) | 3.0% (4.3) | 0% (0 sec.) |
| 18 pmoles | 20% (8.5) | 21% (29.5) | 8.4% (15.3 sec) |
| 1.8 pmoles | 28% (12) | 32% (44.3) | 46% (84.3 sec) |

GSAF II Administration:

With minimal restraint, peptide GsAF II was injected intrathecally (i.th.) into young (75–150 gram) male Sprague-Dawley rats (Charles Rivers Laboratories, Wilmington, Mass.) into the spinal subarachnoid space between lumbar spinous processes L4 and L5 using 10 microliter Hamilton syringes equipped with ⅛ inch by 28G needles. Dosing levels were based upon concentrations deduced from ultraviolet absorbance values at 280 nm as stated previously. Based upon a mass of 3980 Da, 583 pmoles corresponds to 2.3 micrograms of GsAF II, and 2.33 nmoles corresponds to 9.3 micrograms of GsAF II. Injection volume was 10 microliters. The injection vehicle was saline or 0.1% bovine serum albumin(BSA)/saline. The rats were pretreated with GsAF II 15 minutes prior to injection with formalin.

|  | Acute Flinches | Tonic Flinches | Tonic Licking |
| --- | --- | --- | --- |
| Vehicle Control | (16.8) | (86) | (95.0 sec) |
| 2.33 nmoles | 19% (3.25) | 1.4% (1.2) | 0% (0 sec) |
| 583 pmoles | 41% (6.8) | 9.5% (8.2) | 8.2% (7.8 sec) |

In addition to the above analyses, 180 pmoles (666 nanograms) of GsAF I was administered 5 minutes after injection of 5% formalin and the tonic phase responses were recorded as described previously. The highly efficacious activity of GsAF I was retained. Tonic flinch response was inhibited 86% (i.e. 14% of control) and tonic lick duration was reduced 91% (i.e. 9% of control). This property has only been reported for strong analgesic compounds that interact with μ-opioid receptors. It also demonstrates that the analgesic activity of GsAF I is not dependent upon the interruption of the initial rapid firing of sensory fibers (primarily c-fibers) or occlusion of wind-up within dorsal horn neurons.

Example 7

Analgesic Evaluation - Opioid Receptor Testing

In order to determine if the anti-nociceptive effects of GsAF I and II are mediated by opioid receptors, young (75–150 gram) male Sprague-Dawley rats (Charles Rivers Laboratories, Wilmington, Mass.) were pretreated with opioid antagonists at doses that reversed the anti-nociceptive activity of morphine. Animals were then tested in the tail flick test (Example 3) and von Frey tests (Example 5). Subcutaneous administration of 10 mg/kg naloxone 5 minutes prior to the intrathecal administration of 180 picomoles (666 nanograms) GsAF I failed to inhibit the analgesic activity of GsAF I (180 pmoles i.th.) measured 10 minutes later (i.e. 10 minutes post i.th. administration of GsAF I and 15 minutes post subcutaneous administration of naloxone), but completely antagonized the analgesic effect of morphine (3 µg i.th.). Additionally, intrathecal administration of naloxone (50 µg) immediately prior to intrathecal dosing of 180 pmoles GsAF I failed to inhibit analgesic response measured 10 minutes later whereas reversal of intrathecal morphine (3 µg) was determined.

Similarly, pretreatment with the irreversible opioid antagonist B-funaltrexamine (5 micrograms administered intrathecally 18 hours prior to the injection of GsAF I) failed to inhibit the analgesic activity of GsAF I in either the hot plate test (Example 4) or formalin test (Example 6). The analgesic profile for GsAF I, and presumably GsAF II, indicates high efficacy mediated by a non-opioid receptor related mechanism.

Example 8

Analgesic Evaluation for Cross Tolerance of GsAF I with Morphine

Repeated administration of morphine to both humans and rodents results in a decreased analgesic response for any individual dose or a leftward shift in the dose response curve. This phenomenon, termed tolerance, leads to an escalation of morphine dose for maintenance of equivalent pain relief over time. Clinically, the difference in tolerance development for analgesia versus negative side effects (i.e. sedation, constipation, respiratory depression, etc) can limit the utility of morphine in a chronic treatment regime. Although the physiological basis of tolerance is not completely understood, putative analgesic compounds can be evaluated to determine if their efficacy is altered as a result of morphine administration (i.e. morphine cross tolerance). Young (75–150 gram) male Sprague Dawley rats (Charles Rivers Laboratory, Wilmington, Mass.) were subcutaneously dosed twice daily for 6 days with escalating quantities (i.e. 2.5 mg/kg/dose - day 1; 5 mg/kg/dose - day 2; 10 mg/kg/dose - day 3; 20 mg/kg/dose - days 4 and 5; 25 mg/kg/dose - day 6) of morphine or with saline as a vehicle control. On the seventh day, the analgesic activity of morphine and GsAF I was tested using the tonic flinch response of the formalin pain test (as described in Example 6). Dose response determinations for morphine and GsAF I were done using intrathecal administration into young (75–150 gram) male Spraque Dawley rats (Charles River Laboratories, Wilmington, Mass.). With minimal restraint, either morphine or GsAF I was Is injected into the spinal subarachnoid space between lumbar spinous processes L4 and L5 using 10 microliter Hamilton syringes equipped with ⅜ inch by 28G needles. Dosing levels of GsAF I were based upon concentrations deduced from ultraviolet absorbance values at 280 nm using an extinction coefficient of 18710. Injection volumes were 10 ul for both morphine and GsAFI. Vehicle controls for morphine and GsAFI were saline and 0.1% BSA/saline, respectively.

Animals treated with morphine for 6 days and then evaluated for analgesia induction as a result of morphine administration on the seventh day exhibited a significant leftward shift (300x) in the dose response curve versus animals receiving the saline vehicle ($ED_{50}=0.1$ ug i.th. for saline control group; $ED_{50}>30$ ug i.th. for morphine treatment group). $ED_{50}$ is the dose required to give 50% of the maximal analgesic effect.

In contrast, the dose response properties of GsAF I were not significantly different for the two treatment arms of the study ($ED_{50}$–26.7 pmoles i.th. for saline control group; $ED_{50}$–20 pmoles i.th. for morphine treatment group) indicating that prior exposure to morphine does not alter the analgesic properties of GsAF I or produce cross tolerance.

Example 9

Analgesia Evaluation - Acute Inflammatory Pain Testing

Tissue injury results in inflammation and hyperalgesia (i.e. increased magnitude or duration of pain response to supra threshold noxious stimuli) at both the site of injury and at adjacent tissue sites. To assess the anti-hyperalgesic activity of GsAF II in inflammatory pain conditions, paw withdrawal latencies were determined in adult 350–400 gram male Sprague Dawley rats following the unilateral injection of carrageenan, a seaweed extract, into the hindpaw in accordance with the method of Hargreaves et al, Pain, 32:77–88, 1988. Briefly, withdrawal latencies are measured by placing the rat on a glass plate and focusing radiant heat from the underside of the plate toward the hindpaw surface. Latencies values are recorded in seconds to withdrawal of the hindpaw from the surface of the plate. Basal measurements are made prior to injection of the carrageenan (4 mg/hindpaw), followed by a measurement at 150 min post carrageenan injection to obtain the level of hyperalgesic response. Subsequent to the second measurement, GsAF II or vehicle (i.e.0.1% BSA/saline) is administered through an indwelling intrathecal cannula positioned within the lumbar enlargement of the spinal cord. Anti-hyperalgesic activity is determined by measuring paw withdrawal latencies at various time intervals following compound administration. Concurrent with the paw withdrawal latencies, physical measurements of paw volume and paw temperature are recorded to detect anti-inflammatory and anti-pyretic activities.

| Mean Latency Time In Seconds ± SEM | | |
|---|---|---|
| | Vehicle Control (n = 8) | 3 nmol GsAFII (n = 4) |
| Base latency prior to carrageenan injection | 10.12 ± 0.05 | 8.3 ± 1.2 |
| 150 minutes post carrageenan injection | 2.14 ± 0.24 | 3.0 ± 0.81 |
| 30 minutes post treatment | 2.73 ± 0.08 | 17.82 ± 3.78 |
| 60 minutes post treatment | 3.61 ± 0.40 | 20.8 ± 0.00 |

Development of hyperalgesia was detected in all animals tested. As shown in the table above, paw withdrawal times were significantly reduced at 150 min post injection of carrageenan. Administration of 3 nmoles of GsAF II completely reversed this hyperalgesic, thermal-induced response by increasing paw withdrawal latencies to near maximal values (17.82±3.78 sec) at 30 min and to a predetermined cut-off value (20.8 sec) at 60 min. No significant reduction in either paw volume or paw temperature was detected and there was no indication of confounding motor deficits or presence of overt negative side effects. GsAF II is an effective analgesic/anti-hyperalgesic compound for acute peripheral inflammatory pain. GsAF II does not appear to possess anti-inflammatory properties since the induction of analgesia was not associated with an acute reduction of edema or of body temperature.

I claim:

1. A method of treating pain comprising administering to a mammal in need of such treatment an effective analgesic amount of a peptide having the amino acid sequence of SEQ ID. NO.: 1 or SEQ ID. NO.: 2.

2. The method of claim 1 wherein said peptide has the amino acid sequence of SEQ ID. NO.: 1.

3. The method of claim 1 wherein said peptide has the amino acid sequence of SEQ ID. NO.: 2.

* * * * *